US006928437B2

United States Patent
Shibuya et al.

(12) 
(10) Patent No.: US 6,928,437 B2
(45) Date of Patent: Aug. 9, 2005

(54) DATABASE SEARCH DEVICE, DATABASE SEARCH SYSTEM, DATABASE SEARCH METHOD, PROGRAM AND STORAGE MEDIUM

(75) Inventors: Tetsuo Shibuya, Yamato (JP); Hisashi Kashima, Yamato (JP)

(73) Assignee: International Business Machines Corp., Armonk, NY (US)

( * ) Notice: Subject to any disclaimer, the term of this patent is extended or adjusted under 35 U.S.C. 154(b) by 443 days.

(21) Appl. No.: 10/146,342

(22) Filed: May 15, 2002

(65) Prior Publication Data

US 2002/0174115 A1 Nov. 21, 2002

(30) Foreign Application Priority Data

May 15, 2001 (JP) ........................................ 2001-145684

(51) Int. Cl.[7] .............................................. G06F 17/30
(52) U.S. Cl. ............................. 707/6; 707/10; 707/104.1
(58) Field of Search .............................. 707/1, 3, 6, 10, 707/104.1

(56) References Cited

U.S. PATENT DOCUMENTS

| | | | | |
|---|---|---|---|---|
| 5,418,948 A | * | 5/1995 | Turtle ............................. | 707/4 |
| 5,598,350 A | * | 1/1997 | Kawanishi et al. ............ | 702/20 |
| 5,701,256 A | * | 12/1997 | Marr et al. .................... | 702/20 |
| 5,706,498 A | * | 1/1998 | Fujimiya et al. ............... | 707/6 |
| 5,873,082 A | * | 2/1999 | Noguchi ......................... | 707/3 |
| 5,908,755 A | * | 6/1999 | Kumar et al. .................. | 435/6 |
| 5,940,825 A | * | 8/1999 | Castelli et al. ................. | 707/6 |
| 5,977,890 A | * | 11/1999 | Rigoutsos et al. ............. | 341/55 |
| 6,023,659 A | * | 2/2000 | Seilhamer et al. ............. | 702/19 |
| 6,029,167 A | * | 2/2000 | Evans ............................ | 707/4 |
| 6,092,065 A | * | 7/2000 | Floratos et al. ................ | 707/6 |
| 6,108,666 A | * | 8/2000 | Floratos et al. .......... | 707/104.1 |
| 6,189,013 B1 | * | 2/2001 | Maslyn et al. ........... | 707/104.1 |
| 6,303,297 B1 | * | 10/2001 | Lincoln et al. ................. | 435/6 |
| 6,363,399 B1 | * | 3/2002 | Maslyn et al. ........... | 707/104.1 |
| 6,373,971 B1 | * | 4/2002 | Floratos et al. ............. | 382/129 |
| 6,691,109 B2 | * | 2/2004 | Bjornson et al. ............... | 707/4 |
| 6,785,672 B1 | * | 8/2004 | Floratos et al. ................ | 707/3 |

OTHER PUBLICATIONS

Altschul, Steven et al., Issues in Searching Molecular Sequence Databases, Nature Genetics, vol. 6, Feb. 1994, pp. 119–129.*

* cited by examiner

*Primary Examiner*—Luke S Wassum
*Assistant Examiner*—Susan Rayyan
(74) *Attorney, Agent, or Firm*—Richard M. Goldman (57) ABSTRACT

A method is provided for allowing a database search that prevents an owner of the database or someone intercepting the database search in the network from knowing the contents of the query, without requiring any particular processing on the part of the database. Client 20 accesses database server 10 which stores sequence patterns and inquires whether the sequence patterns stored in the database server 10 exist in a predetermined sequence. Client 20 comprises sequence processing section 21 for dividing a search sequence subjected to search to create multiple subsequences; and query issuing section 22 for issuing a query to database server 10 using the created multiple subsequences individually as a query sequence.

11 Claims, 12 Drawing Sheets

| | A1 | E1, 3 | A3 |
|---|---|---|---|
| D1, 3 | | | |

| | A1 | E1, 4 | A4 |
|---|---|---|---|
| D1, 4 | | | |

. . . . . . . .

| | A1 | E1, q−1 | Aq−1 |
|---|---|---|---|
| D1, q−1 | | | |

| | A1 | E1, q | Aq |
|---|---|---|---|
| D1, q | | | |

```
A . . . LV . . GV . . . L
A . . . NA. SL . . . L
A . . I . . . . L . . . VSY
A . . L . . L . IAL
DE . . . . . K . . KK. L
D . . . . . E. LK. AK
D . . . . . . . LKK . . EK
D . . . . . . . . . AKEKG
E. IK. AK . . . . . I . . . LFL . . . . LLS. KK. L . . KLL
E . . KK . . EK . . . . E
E. LK. AKE
E . . LG. K . . K . . L
E . . R . . KN . . . LF
E . . . . . K . . GAD. V
FKN . . . . L . . . . L. L
F . . . . . GL . . G. L. L . . . V. G. K. KAGK. I
KE. LE . . . . . . LK
KE . . E . . . . Q . . K. I
KL. E . . S . . . K . . L
KT. LT . . . . EEGGRE. K . . . ELF. ELSPLS
K . . . KGL . . . SL
LFL . . . . . . LLS
LG. A . . . . I . . . G. L
LKT. L. I. S
LK . . KE . . . . I. E
LLVI . . . . . . F . . . S
LL. IS . . L . . . . . . L
L. F . . FKK. L
L. L . . L . . A . . . EI
L. S . . . . AL. L . . L
L. LL . . . L . . . . . SL
L. L. S. LLF
L. PLLF . . . . . L
L. SP . . . . . EK. L
L . . SL. L . . F . . L
L . . . D. K . . . . KN. K
L . . . . EKSL . . K
L . . . . S. GL . . . L. I
L . . . . . L . . . SPLL
L . . . . . KKG . . . G. L
N . . KE. LE . . . . . . L
P. DIE . . . G . . KGR . . . . A. K . . . F . . FP
SL. L . . F . . L . . I
SL . . . KE. L. E
S . . S . . . . KE. LE
V. E. LEE . . . . . . K
V . . . L. A . . . A. VL
```

Fig. 8

```
MLIAVPLDDTNFSENMLIAVPLDDTNFSENLKKAKEKGADIVELRVDQFSDTSLNYVKEK
LEEVHSQGLKTILTIRSPEEGGREVKNREELFEELSPLSDYTDIELSSRGLLVKLYNITK
EAGKKLIISYHNFELTPPNWIIREVLREGYRYGGIPKIAVKANSYEDVARLLCISRQVEG
EKILISMGDYGKISRLAGYVFGSVITYCSLEKAFAPGQIPLEEMVELRKKFYRL
```

Fig. 9

```
D. . . . . E. LK. AK
D. . . . . . . LKK. . EK
D. . . . . . . . . AKEKG
E. LK. AKE
E. . KK. . EK. . . . . E
E. . R. . KN. . . LF
E. . . . . K. . GAD. V
KE. LE. . . . . . LK
KE. . E. . . . Q. . K. I
KL. E. . S. . . K. . L
KT. LT. . . . EEGGRE. K. . . ELF. ELSPLS
LKT. L. I. S
LK. . KE. . . . I. E
L. . . . S. GL. . . L. I
N. . KE. LE. . . . . . L
SL. . . KE. L. E
S. . S. . . . KE. LE
V. E. LEE. . . . . . K
```

Fig. 10

1) MLIAVPLDDTNFSENMLIAVPLDDTNFSENLKKAKEKGADIVELRVDQFSDTSLNYVKEK
2) LKKAKEKGADIVELRVDQFSDTSLNYVKEKLEEVHSQGLKTILTIRSPEEGGREVKNREE
3) LEEVHSQGLKTILTIRSPEEGGREVKNREELFEELSPLSDYTDIELSSRGLLVKLYNITK
4) LFEELSPLSDYTDIELSSRGLLVKLYNITKEAGKKLIISYHNFELTPPNWIIREVLREGY
5) EAGKKLIISYHNFELTPPNWIIREVLREGYRYGGIPKIAVKANSYEDVARLLCISRQVEG
6) RYGGIPKIAVKANSYEDVARLLCISRQVEGEKILISMGDYGKISRLAGYVFGSVITYCSL
7) EKILISMGDYGKISRLAGYVFGSVITYCSLEKAFAPGQIPLEEMVELRKKFYRLHRRAMK

Fig. 11

```
D.....E.LK.AK
D......LKK..EK
D........AKEKG
E.LK.AKE
E..KK..EK....E
E.....K.GAD.V
LK..KE....I.E
```

Fig. 12

8) EKAFAPGQIPLEEMVELRKKFYRLHRRAMKMLIAVPLDDTNFSENMLIAVPLDDTNFSEN

Fig. 13

```
A = MLIAVPLDDTNFSENMLIAVPLDDTNFSEN
B = LKKAKEKGADIVELRVDQFSDTSLNYVKEK
C = LEEVHSQGLKTILTIRSPEEGGREVKNREE
D = LFEELSPLSDYTDIELSSRGLLVKLYNITK
E = EAGKKLIISYHNFELTPPNWIIREVLREGY
F = RYGGIPKIAVKANSYEDVARLLCISRQVEG
G = EKILISMGDYGKISRLAGYVFGSVITYCSL
H = EKAFAPGQIPLEEMVELRKKFYRLHRRAMK
```

Fig. 14

```
I = LKSVIANAEQKGLDLDRLYIKKAVADDGPI
```

Fig. 15

| Position | 1 | 2 | 3 | 4 | 5 |
|---|---|---|---|---|---|
| A | 10% | 10% | 80% | 20% | 50% |
| T | 20% | 0% | 10% | 20% | 50% |
| C | 30% | 40% | 0% | 40% | 10% |
| G | 40% | 50% | 10% | 20% | 15% |

Fig. 16

DATABASE SEARCH DEVICE, DATABASE SEARCH SYSTEM, DATABASE SEARCH METHOD, PROGRAM AND STORAGE MEDIUM

BACKGROUND OF THE INVENTION

1. Field of the Invention

The present invention relates to a database search method, and more particularly to a database search method capable of hiding search objects from anyone except for a client who issues a query.

2. Related Art

Recently, much genetic information such as DNA, has been figured out and its results are stored in a variety of databases such as a motif database. Consequently, as for the analysis results of DNA, one can search related information using these databases.

For example, a motif database is the one that collects various patterns relating to functions of DNA and protein, etc. This database stores patterns such as the following.

A..T..ATAT...CGATGA (".." represents any character)
A..[AT]..ATCG.A ("[AT]" represents A or T)

Therefore, collating DNA analysis results, one can find what patterns the analysis results contains, that is, what functions associated DNA holds.

On the other hand, it is often the case in such database search that the query includes private information or confidential information about research and development, thus a leak of such information is worried about. Conventionally, in order to prevent a leak of information in database search, a method has been used for encrypting data relating to a query or a search technique called private information search.

As described above, when performing database search using published databases, information contained in a query might leak so that there exists a need for means to effectively prevent a leak of information.

As one of search methods that use encrypted data to prevent a leak of information, there is one that transmits a query including encrypted data to a database, where the encrypted data is decoded before search processing is performed and then the results are returned. In this regard, there exist various techniques for encryption.

However, since this method needs a function to decode encrypted data on the part of a database, it takes a lot of trouble with introduction.

Furthermore, as an owner of the database knows the contents of the query, there remains a likelihood that information leaks.

On the other hand, private information search is a method where a query is issued without informing an entry of a database that is desired to be known. Accordingly, this method theoretically assures the security in terms of information theory and prevents a leak of information completely.

However, this method involves particular operations on the database during a procedure, thus the database needs to be constructed in accordance with this search method. Therefore, a lot of trouble is again required with introduction.

In addition, since it is essential for the security that all of the entries of the database are referenced once, this method is impractical for large scale databases because a great amount of search time is required.

Besides there is inconvenience in that ambiguous search is not allowed that is essential for dealing with data sequence matching.

SUMMARY OF THE INVENTION

In view of those problems described above, it is an object of the present invention to provide a method for allowing database search that prevents an owner of the database or someone intercepting the database search halfway through the network from knowing the contents of a query, without requiring any particular processing on the part of a database.

For achieving the above object, the present invention is directed to a database search device for accessing a database that stores sequence patterns and inquiring whether the sequence patterns stored in the database exist in a predetermined sequence, the device comprising: a sequence processing section for dividing a search sequence subjected to search to create multiple subsequences; and a query issuing section for issuing a query to the database using the created multiple subsequences individually as a query sequence.

The sequence processing section may overlap a predetermined length of sequence elements depending on a length of the sequence patterns stored in the database to create the multiple subsequences.

In this way, by providing overlapping portions, it is possible in database search to prevent overlooking detection of a sequence pattern that exists extending over subsequences.

The sequence processing section may create a sequence by connecting a sequence element of an end portion of the search sequence and a sequence element of a head portion of the search sequence and add to the subsequences.

Adding such a sequence and issuing a query along with the subsequences, if someone who does not know an original search sequence attempts to restore that original search sequence from the subsequences, he or she can not tell which subsequence lies at the head, thus the security is enhanced.

Furthermore, the sequence processing section may create a dummy sequence that does not contribute to database search associated with the search sequence and add to the subsequences.

What is used as a dummy sequence would be a sequence in which overlapping portions of the multiple subsequences are mixed, a sequence that has the same overlapping portions as the subsequences and in which any sequence elements are inserted into non-overlapping portions, or a sequence composed of any sequence elements and having the same length as the subsequences.

In another aspect of the invention, there is provided a database search device, comprising: a sequence processing section for connecting any sequence to a search sequence subjected to search; and a query issuing section for issuing a query to a database using the sequence obtained by the sequence processing section as a query sequence.

It is noted that a sequence connected to the search sequence may be any other search sequence or a meaningless dummy sequence. Connecting multiple sequences to the search sequence makes it possible to hide the search sequence serving as an essential objective for database search.

Furthermore, the sequence processing section may create multiple subsequences with dividing the sequence obtained by connecting any sequence to the search sequence. In this case, the query issuing section issues queries to the database using the multiple subsequences as a query sequence.

Such a scheme for connecting the multiple sequences before dividing makes it much more difficult to restore an original search sequence.

In a further aspect of the invention, there is provided a database search device, comprising: means for making an inquiry multiple times to a database about a search sequence subjected to search, each of the inquiries corresponding to each of predetermined portions of the search sequence; and means for receiving search results from the database and extracting information corresponding to the search sequence from the search results.

The inquiry means described above may overlap a predetermined length of sequence elements depending on a length of sequence patterns stored in the database to create multiple subsequences of the search sequence, and make an inquiry to the database for each of the created subsequences.

In a yet further aspect of the present invention, there is provided a program for controlling a computer and for performing the method steps for each component of the aforementioned database search device. This program may be distributed by means of being stored on magnetic storage media, optical storage media, semiconductor memories or other storage media, or may be delivered from a storage device of a program transmission apparatus via a network.

In a still further aspect of the present invention, there is provided a database search system, comprising: a database server provided on a network for storing predetermined sequence patterns; and a client for making an inquiry about search to the database server via the network, wherein the client divides a search sequence subjected to search and sends a query to the database server for each of the divided sequences, and wherein the database server performs database search in response to the received query and sends back search results to the client.

In another aspect of the present invention, there is provided a database search method for accessing a database that stores sequence patterns and inquiring whether the sequence patterns stored in the database exist in a predetermined sequence, the method comprising the steps of: dividing a search sequence subjected to search to create multiple subsequences; issuing a query to the database using each of the created multiple subsequences as a query sequence; and receiving search results from the database and extracting information corresponding to the search sequence from the search results.

Furthermore, the database search method comprises the step of creating a dummy sequence that does not contribute to database search associated with the search sequence prior to the query issuing step, and wherein the query issuing step comprises the step of issuing a query to the database using the dummy sequence as a query sequence.

The subsequence creating step comprises the steps of: connecting any sequence to the search sequence to create a new sequence prior to dividing the search sequence; and dividing the created new sequence to create the multiple subsequences.

DESCRIPTION OF THE PREFERRED EMBODIMENTS

Now the present invention will be described with respect to the embodiment shown in the accompanying drawings.

In the embodiment, database search is to be detect a specific sequence or pattern from a certain length of sequence. Namely, a database stores sequences or patterns with an adequately short length compared with a sequence subjected to a query (hereinafter referred to query sequence), wherein the search is to check to see whether there is an identical or similar sequence or pattern to those stored in the database within the query sequence.

More specifically, a query sequence may be, for example, a base sequence of DNA, wherein a pattern of the base sequence stored in the motif database of genes is detected. In general, the length of motifs in the motif database of genes may be about 4 to 40 bp, while the length of query sequences subjected to search may be 1 bp to several Mbp, thus this example is well suited to consideration.

Figure 1:
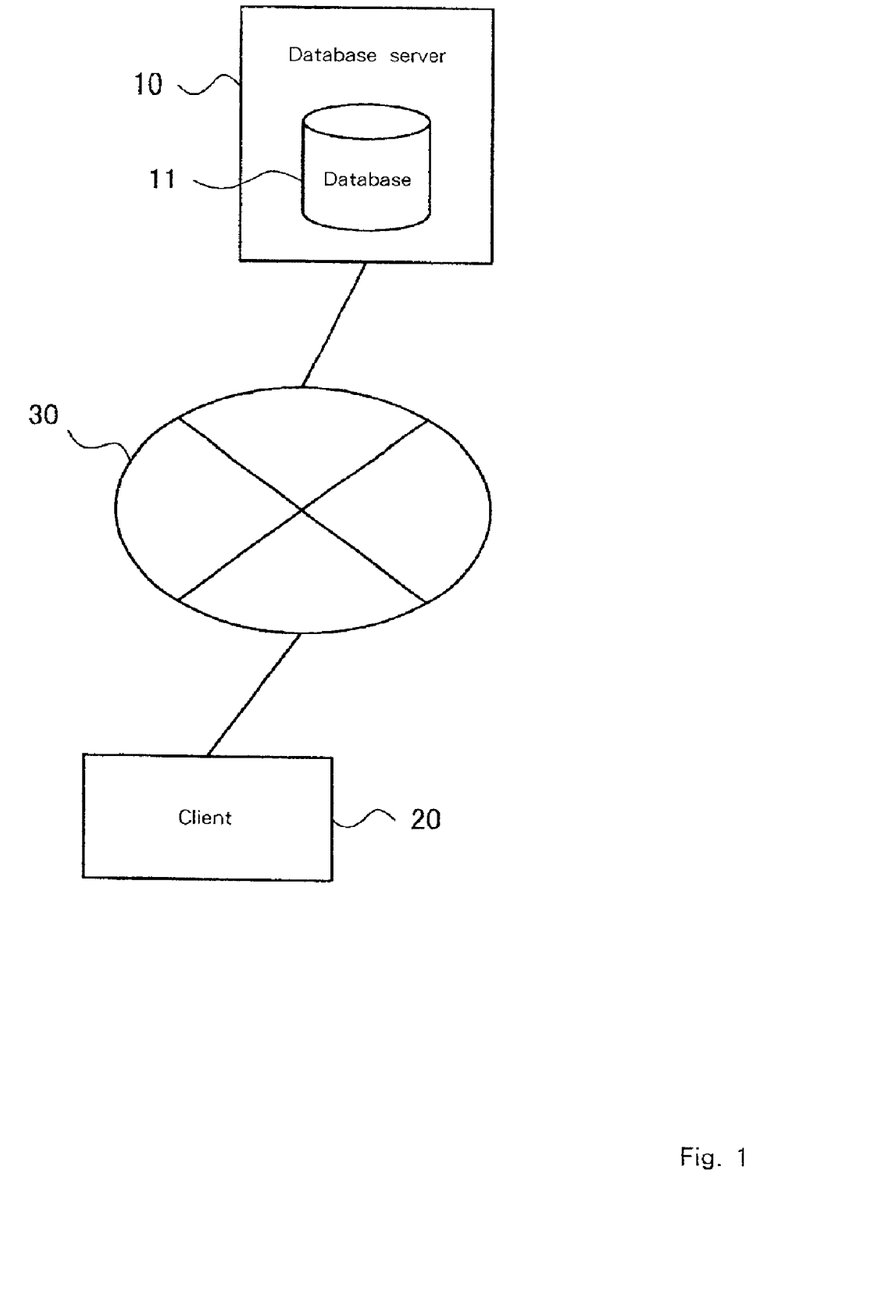
FIG. 1 depicts a schematic diagram of a database search system where database search according to the present invention is implemented.

FIG. 1 depicts a schematic diagram of a database search system where database search according to the present invention is implemented.

As shown in FIG. 1, the database search system of the present invention comprises a database server 10 provided on a network 30 such as the Internet and a client 20 serving as a database search device that accesses database server 10 via network 30 to perform search.

Database server 10 is implemented using a computer such as a workstation or personal computer and is equipped with a database 11 subjected to search according to the invention.

It is now described about database 11 that is used for the present invention. As described above, the present invention is directed to detecting a specific sequence or pattern from a certain length of sequence. Accordingly, database 11 stores this specific sequence or pattern. For example, the following databases are conceivable:

(a) Sequence Database

A database storing relatively short sequences. For example, a database of promoter sequences of DNA, RNA, protein, etc.

(b) Motif Database

A database storing various patterns (motifs) associated with functions of DNA or protein. This database stores such patterns as the following:

A..T..ATAT...CGATGA ("." represents any character)

A..[AT]..ATCG.A ("[AT]" represents A or T)

(c) Matrix Database

Figure 16:
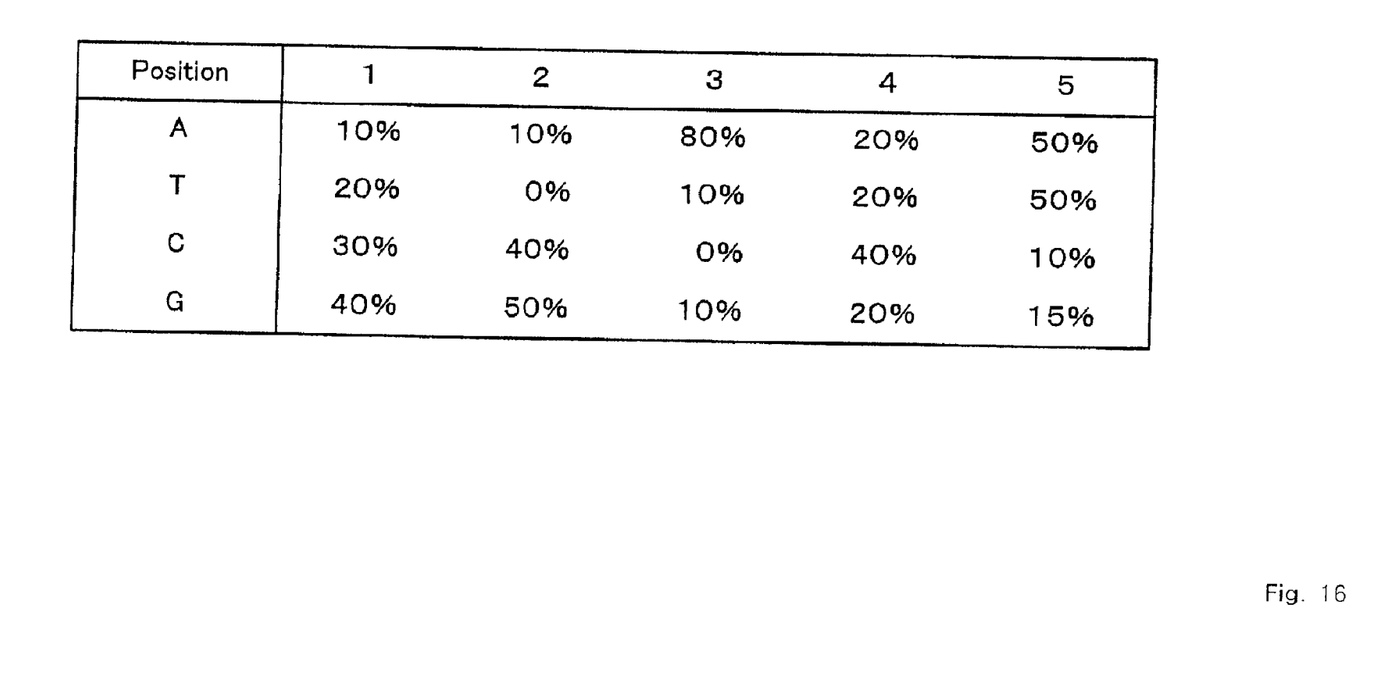
FIG. 16 depicts an example of matrix database.

A database in which an appearance probability of each base at respective positions corresponding to a certain length of sections is represented in a matrix form. FIG. 16 depicts an example pattern stored in a matrix database.

(d) HMM Database

A database storing motifs represented by a hidden Markov model. It is noted that the length is preferably limited to an upper limit when used in the embodiment of the present invention.

Figure 2:
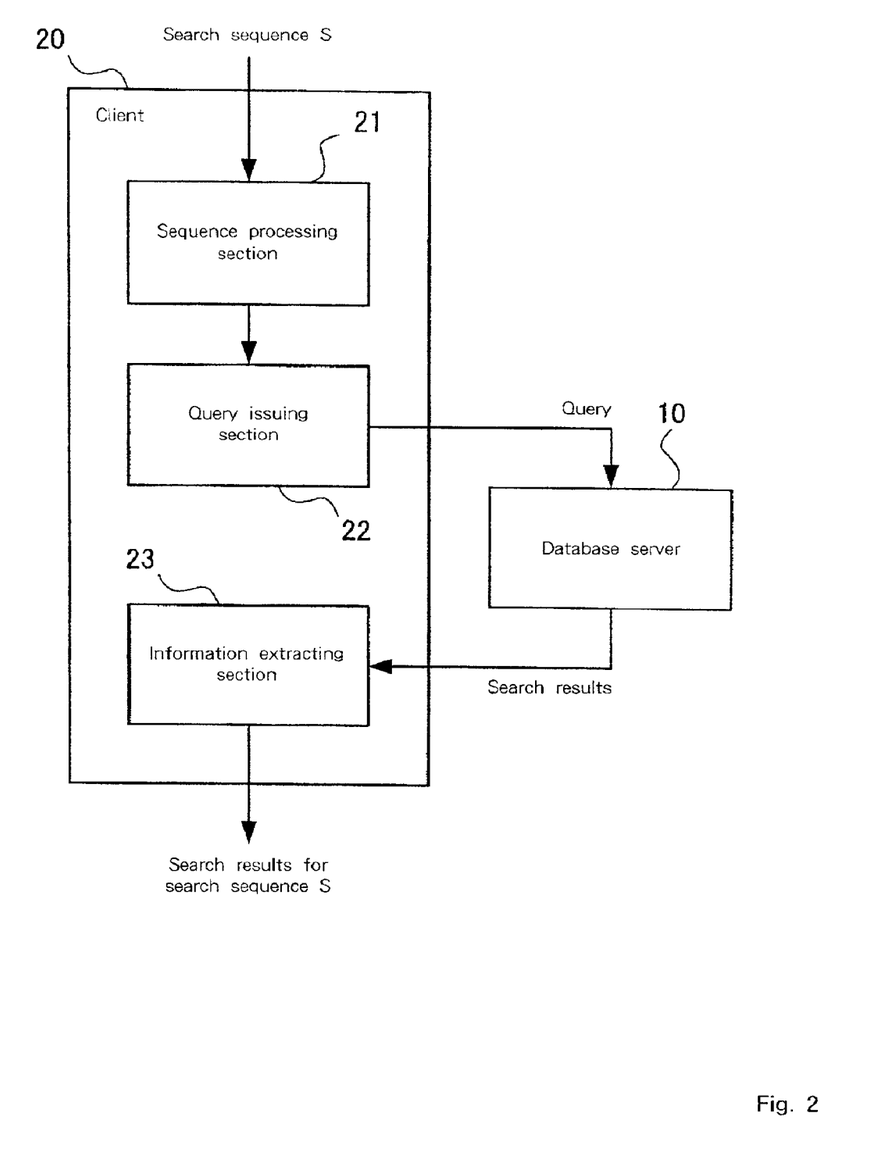
FIG. 2 is a schematic diagram illustrating a client.

FIG. 2 is a schematic diagram illustrating client 20 shown in FIG. 1.

Client 20 accessing database server 10 as described above, which is implemented using a workstation or personal computer, comprises a sequence processing section 21 for processing a sequence (a search sequence) subjected to search to create a query sequence; a query issuing section 22 for issuing a query to database server 10; and information extracting section 23 for receiving search results for the query issued from query issuing section 22 and extracting necessary information.

Sequence processing section 21, query issuing section 22 and information extracting section 23 shown in FIG. 2 are virtual software blocks implemented by a CPU that is controlled by a computer program. The computer program controlling the CPU may be distributed by means of being stored on a storage medium such as a CD-ROM and floppy disk or may be delivered via a network.

Sequence processing section 21 inputs and processes a search sequence. It is noted that sequence processing section 21 processes the search sequence such that an owner of database server 10 or someone who intercepts the query or its response halfway through the network 30 are unable to know an original search sequence prior to processing. The details of processing will be described later.

Query issuing section 22 creates a query using the search sequence created by sequence processing section 21 as a query sequence, and then make an inquiry to database server 10 via network 30.

Information extracting section 23 receives and analyzes a response to the query issued from query issuing section 22 from database server 10, and extracts and outputs information corresponding to search results for the original search sequence. The search results for the original search sequence are obtained by analyzing and processing the response from database server 10 using a technique dependent on how to process the search sequence in query issuing section 22.

Next, it will be described about how to process the search sequence in sequence processing section 21.

(1) Division of a Search Sequence

An original search sequence is able to be hidden by dividing the search sequence into multiple subsequences and performing database search for each of the subsequences. It is now described how to divide the query sequence in detail.

When performing whole matching search for a predetermined sequence or pattern, it assumes that the length of the longest sequence or pattern stored in database 11 of database server 10 is m. On the other hand, when performing homology search, a maximum value of the length of similar portions in sequences having allowed homology is considered and its length is assumed to be m.

Then assuming that a sequence (e.g., character string) subjected to database search is S[0 . . . n], division is performed as follows:

S=A1 B1 A2 B2 A3 B3 . . . AK-1 BK-1 AK where Ai and Bi (i=1, 2, 3, . . . , k-1, k) are a partial character string as a sequence element of the sequence S, wherein Ai is a partial character string with a length of more than or equal to m-1 and Bi is a partial character string with any length (including an empty space). For such a divided sequence S, the following k-1 sequences, C1, C2, . . . , Ck-1, are defined as query sequences to perform database search.

C1=A1 B1 A2

C2=A2 B2 A3

. . .

Ck-1=Ak-1 Bk-1 Ak

Namely, the sequence S is divided into a series of query sequences, each of which has only at its head portion and end potion a character string with a predetermined sequence or pattern in database 11 in an overlapping manner, and database search is performed for each of these individual query sequences. This allows to obtain the same search results as when doing database search with respect to the sequence S.

Figure 3:
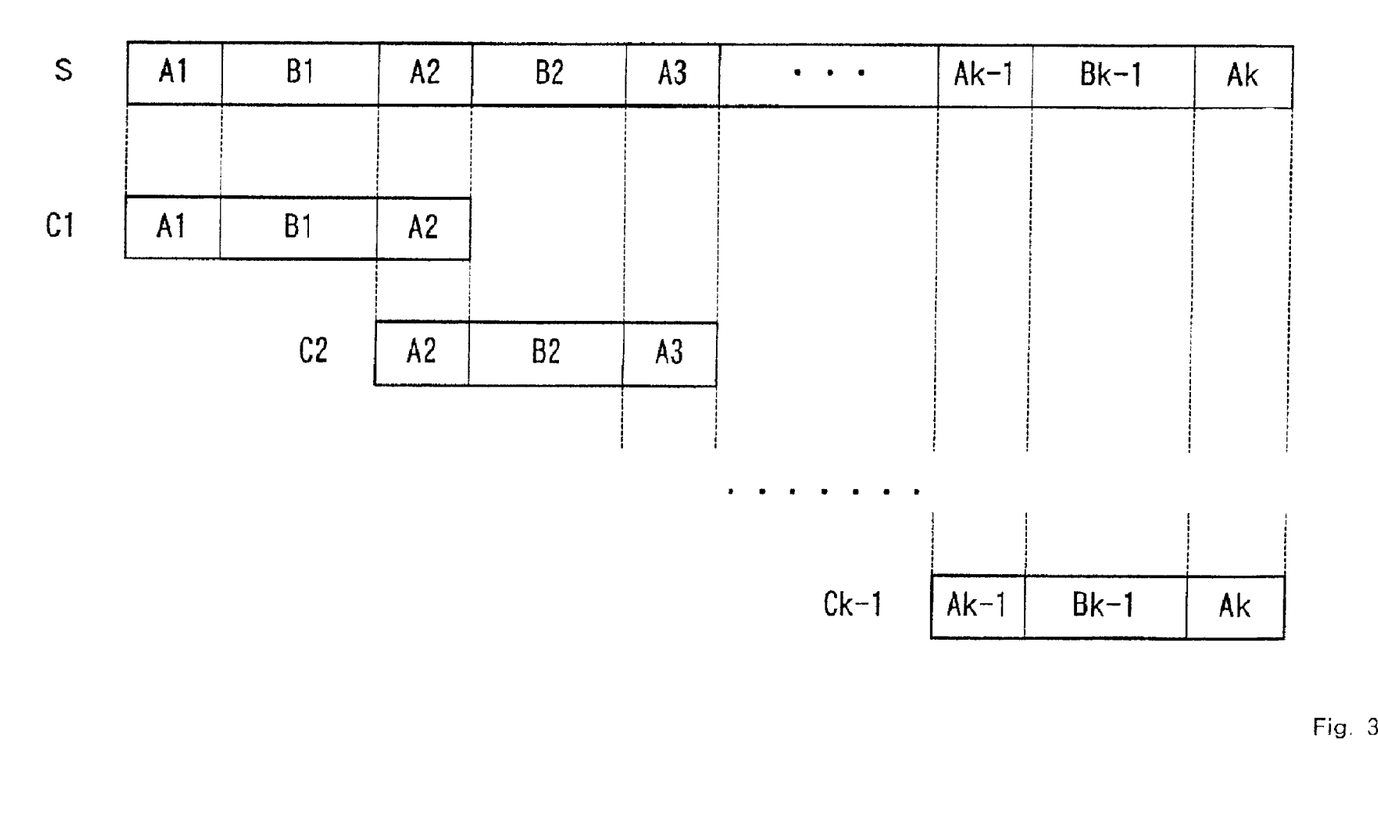
FIG. 3 depicts a relationship between search sequence S and sequences C1, . . . , Ck-1 that are created by dividing this sequence S.

FIG. 3 depicts a relationship between search sequence S and sequences C1, . . . , Ck-1.

It is noted that the number of characters of query when using these sequences C1, . . . , Ck-1 is twice at the most as much as when searching the original sequence S as it is (i.e., twice is when all of the partial character strings B1, . . . , Bk-1 are empty sets).

In this manner, dividing a sequence subjected to database search such that predetermined conditions are met and then performing database search using the obtained individual subsequences as a new query sequence, the same search results are able to be obtained as in the database search using an original query sequence with keeping the original sequence serving as an essential object unknown to someone who intercepts the individual database searches.

However, even in this case, it is unfortunately possible for an owner of database 11 or someone who intercepts on the network 30 to know the original sequence by collecting all the information about the queries corresponding to each of the subsequences. Accordingly, security is not necessarily ensured. Therefore, according to the embodiment of the invention, the divided query sequences described above are further processed.

(2) Adding a Sequence that Hides the Head Portion of a Query Sequence

Along with the query sequences C1, . . . , Ck-1 based on the subsequences obtained by dividing the original sequence S, the following sequence, that is, Ck=Ak Bk A1 is used as a query sequence to perform database search. Note that a character string Bk may be any sequence, including an empty sequence.

Figure 4:
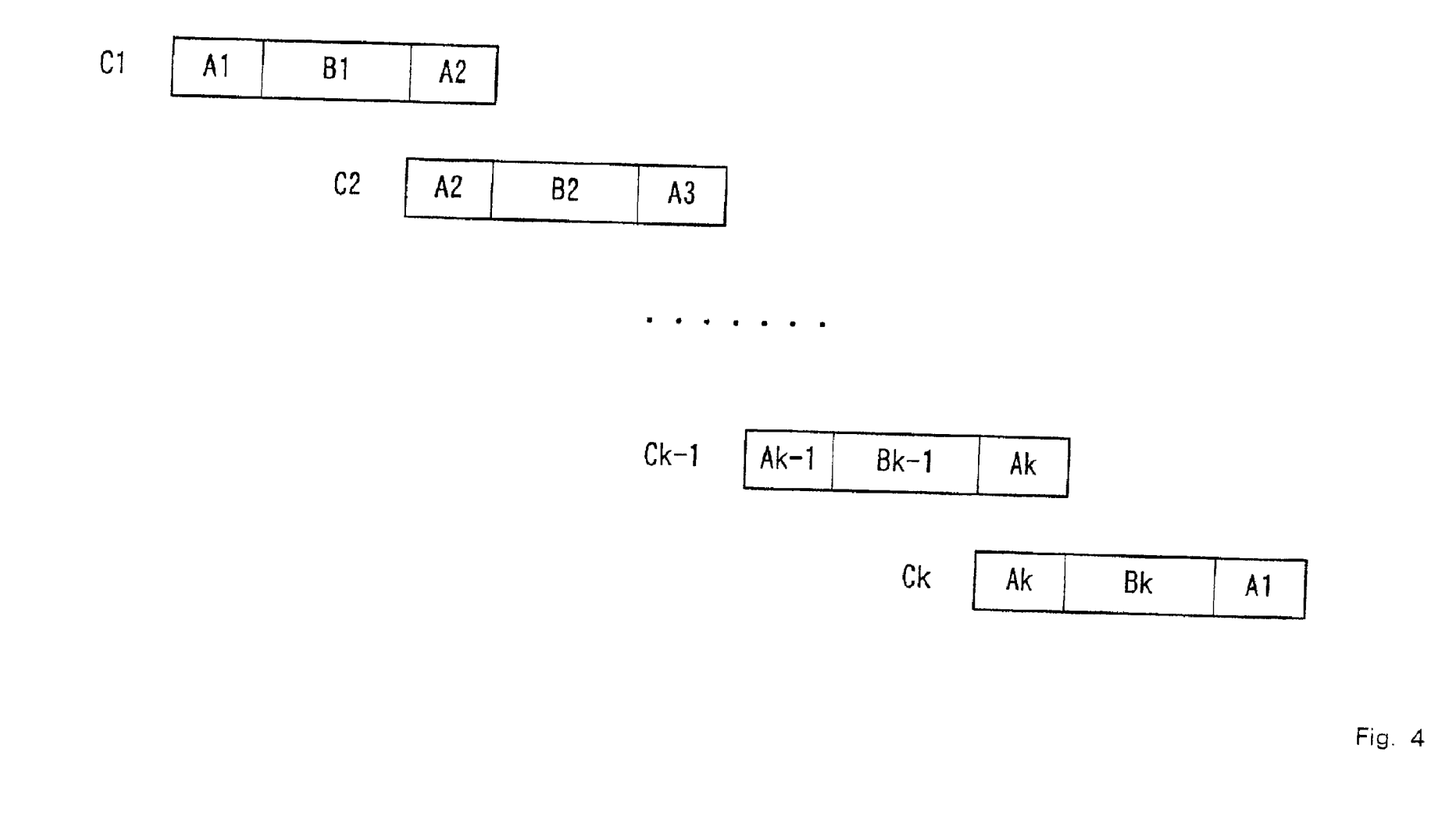
FIG. 4 illustrates that a query sequence Ck is appended to query sequences C1, . . . , Ck-1 shown in FIG. 3.

FIG. 4 illustrates that a query sequence Ck is appended to query sequences C1, ..., Ck-1 shown in FIG. 3.

This means adding a subsequence in which the end portion of the original sequence S is connected to the head portion of the same. This addition makes it unknown which query sequence corresponds to the head portion of the original sequence even if collecting all of the k query sequences from the information about queries. Accordingly, it becomes difficult for an owner of database 11 or someone who intercepts on network 30 to construct the original sequence S.

However, even in this case, when there is no character string with the same element among the character strings Ai in the query sequences, it may be possible to specify the order of each of the query sequences, therefore, if one constructs all the sequences each of which has as its head portion each query sequence, the original sequence S is to be included among them.

(3) Addition of a Sequence

For the character string of the original sequence S, consider the following sequence Dp,q for all Ap, Aq (p+1 !=q):
Dp,q=Ap Ep,q Aq
where Ep,q is any sequence, including an empty sequence. The number of sequences Dp,q is k(k-1).

Figure 5:
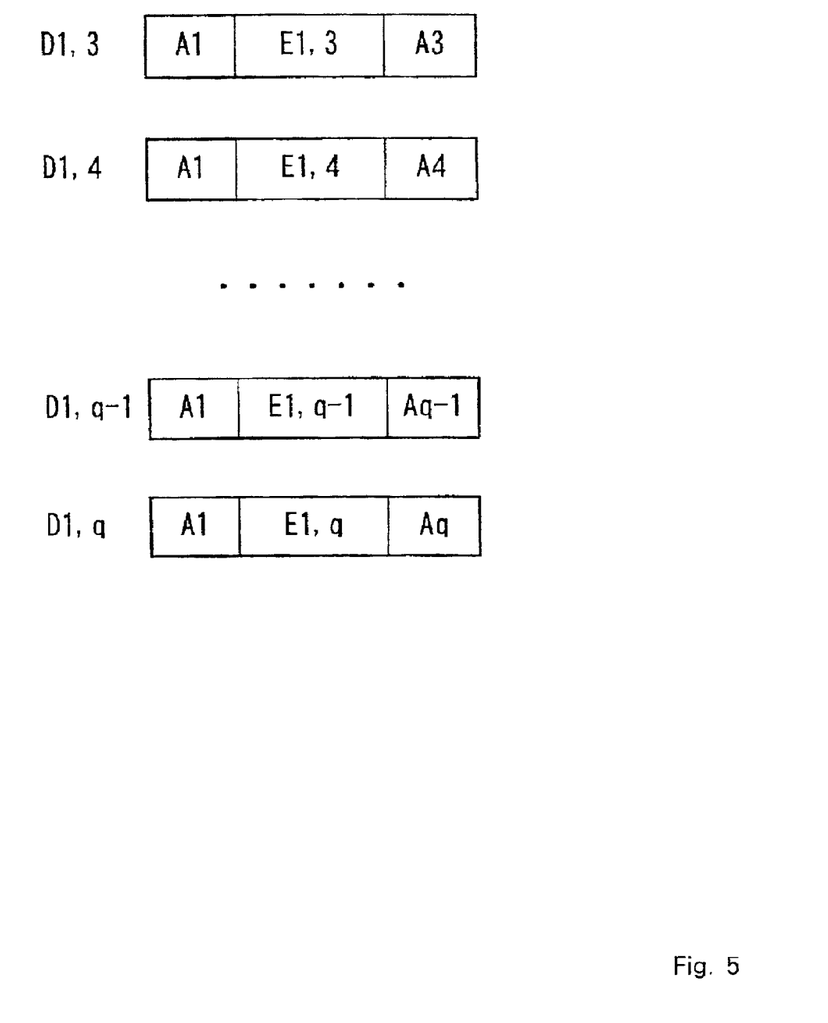
FIG. 5 depicts an example sequence to be added to query sequences C1, . . . , Ck-1 shown in FIG. 3.

FIG. 5 depicts the above sequence D1,q (=A1, E1, q, Aq) associated with a partial character string A1 among the partial character strings A1, ..., Ak for sequence S.

When issuing a query to database server 10, the aforementioned sequence Dp,q is added as a query sequence to the sequences C1, ..., Ck-1 that are obtained by dividing the original sequence S as described in the previous section (1). This makes the number of combinations of the sequences that could be constructed by arranging each of the query sequences enormous, that is, k! even when there is no character string with the same element among the character strings Ai in the query sequences. Accordingly, only if the value of k is large enough, it is nearly impossible to restore the original sequence S.

Needless to say, when there is a character string with the same element among the character strings Ai in the query sequences, it becomes much more difficult to restore the original sequence S.

It is noted that the number of added sequences as a query sequence was k(k-1) in the above technique, however, the added sequences may be decimated appropriately. For example, adding the following sequence Fq makes it more difficult to restore the original sequence S just like the case where sequences Dp,q are added.
Fp=Ap Gp Ap+2
(Note that Ap+2 represents Ap+2-k if p+2>k. Gp is any sequence.)

In this case, if there is no character string with the same element among the character strings Ai in the query sequences, the number of combinations of the sequences that could be constructed by arranging each of the query sequences is $2^{(k-2)/2}$, wherein it is extremely difficult to restore the original sequence S if the value of k is large enough.

(4) Addition of an Alternative Sequence

For a character string Ap in the original sequence S, consider the following sequence Hp for all "p":
Hp=Ap B'p Ap+1
(where B'p is any sequence different from Bp.)

Namely, a sequence having no relation to the original sequence S is included as a dummy sequence in a query. According to this, when there is no character string with the same element among the character strings Ai in the query sequences, the number of combinations of the sequences that could be constructed by arranging each of the query sequences is $2^{k/2}$, therefore, it is extremely difficult to restore the original sequence S if the value of k is large enough.

(5) Connecting Multiple Query Sequences

If there are multiple sequences subjected to database search, one can connect query sequences of these to create one sequence and then apply the above techniques (1) through (4) to this sequence. For example, assuming the sequences subjected to database search are sequences S and T, a sequence S+T is to be created by connecting them. Then after performing processing such as division and addition of sequences as described above to the sequence S+T, creates multiple query sequences and queries are issued.

It is noted that a subsequence that is created by dividing the sequence S+T according to the above technique (1) and includes a boundary between sequence S and sequence T may include the search results for both sequences S and T. Therefore, in order to obtain correct search results for sequence S and sequence T, it is necessary to separate the search results for sequence S and those for sequence T after acquiring the search results.

As for the present technique above, even if the original sequence S+T could be restored by synthesizing and processing duplicate query sequences, this sequence itself has no meaning (namely, what has its meaning is sequence S and sequence T, and an owner of database 11 or someone who intercepts on the network 30 does not know that the sequence S+T is created by connecting these sequences). Accordingly, the security of the sequence S+T, which is subjected to database search by an issuer of queries, is much more enhanced.

Furthermore, generalizing this technique, it is possible to provide and connect any dummy sequences T and U for a sequence S subjected to database search to create a sequence T+S+U and then to create query sequences using the aforementioned techniques (1) through (4).

Moreover, when an original sequence S can not be detected from a new sequence that is created by connecting multiple sequences, a query may be issued using this new sequence as a query sequence without using the aforementioned techniques (1) through (4).

Each of the methods described above for directing to hide a sequence subjected to database search is based on dividing the sequence using the technique (1) and is implemented by any combination of techniques (2) through (5).

If an original sequence S contains exactly the same partial character strings with the length of more than or equal to m-1 when dividing the sequence using the technique (1), such partial character strings may be selected as a part of character string Ai described above. According to this, multiple query sequences created is to contain multiple ones that have the same end character string. This increases greatly the kinds of sequences created by synthesizing multiple queries, thereby making it much more difficult to restore the original sequence S.

The operations of a database search will now be described according to the invention.

Figure 6:
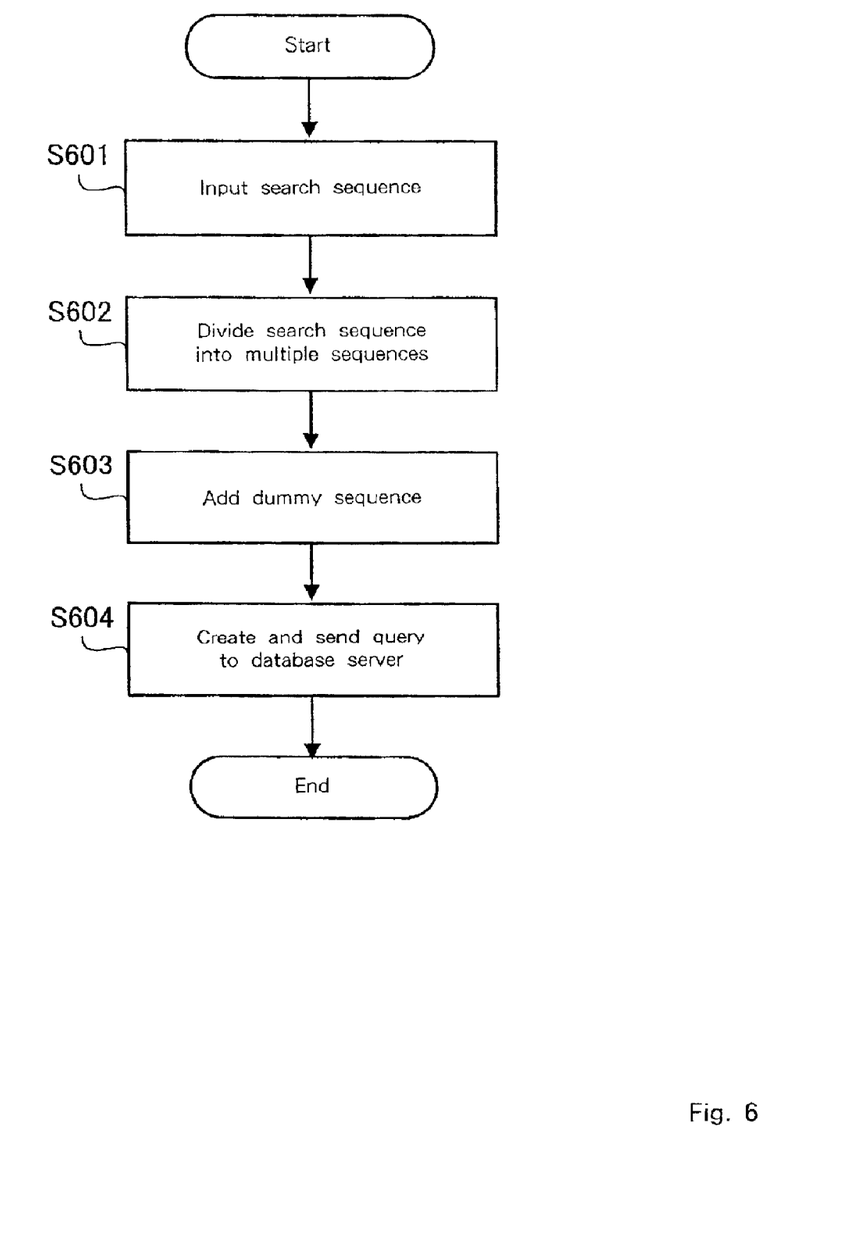
FIG. 6 is a flowchart illustrating operations of sequence processing section 21 and query issuing section 22 shown in FIG. 2.

FIG. 6 is a flowchart illustrating operations of sequence processing section 21 and query issuing section 22 shown in FIG. 2, which serves as inquiry means to database server 10, performing processing described above on the search sequence and issuing queries.

Figure 7:
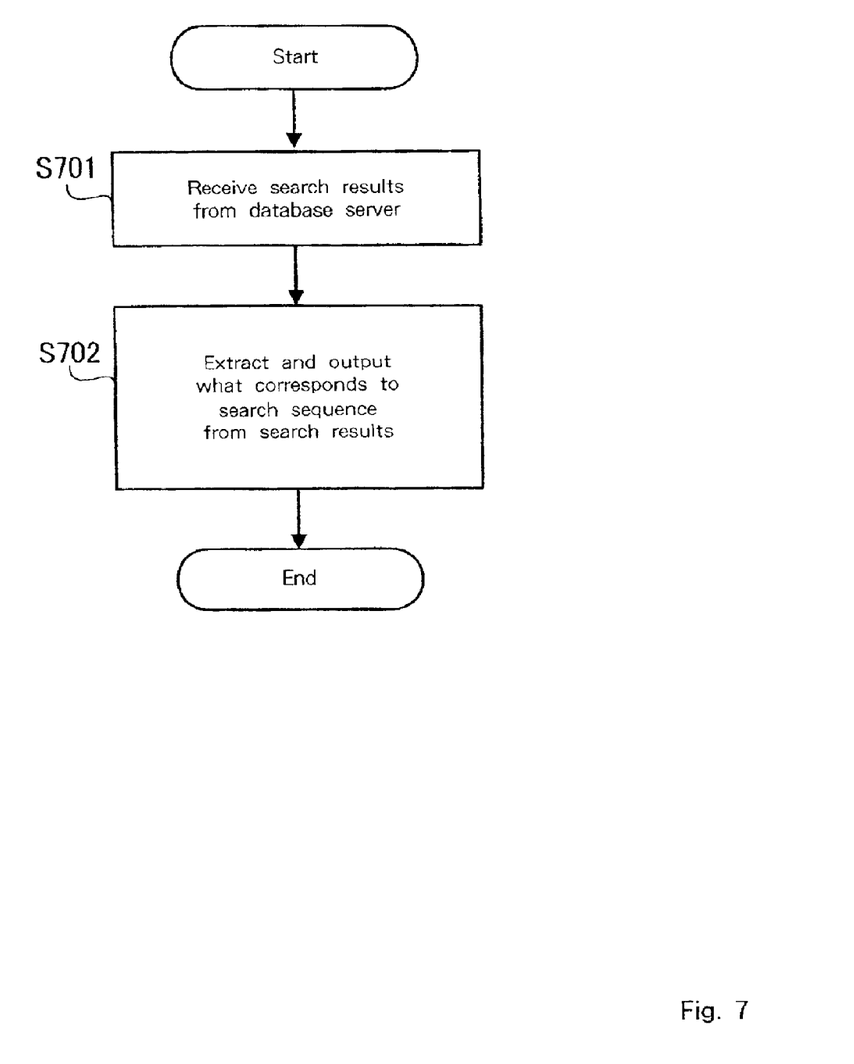
FIG. 7 is a flowchart illustrating operations of information extracting section 23 shown in FIG. 2.

FIG. 7 is a flowchart illustrating operations of information extracting section 23 in receipt of search results as a response from database server 10.

Figure 8:
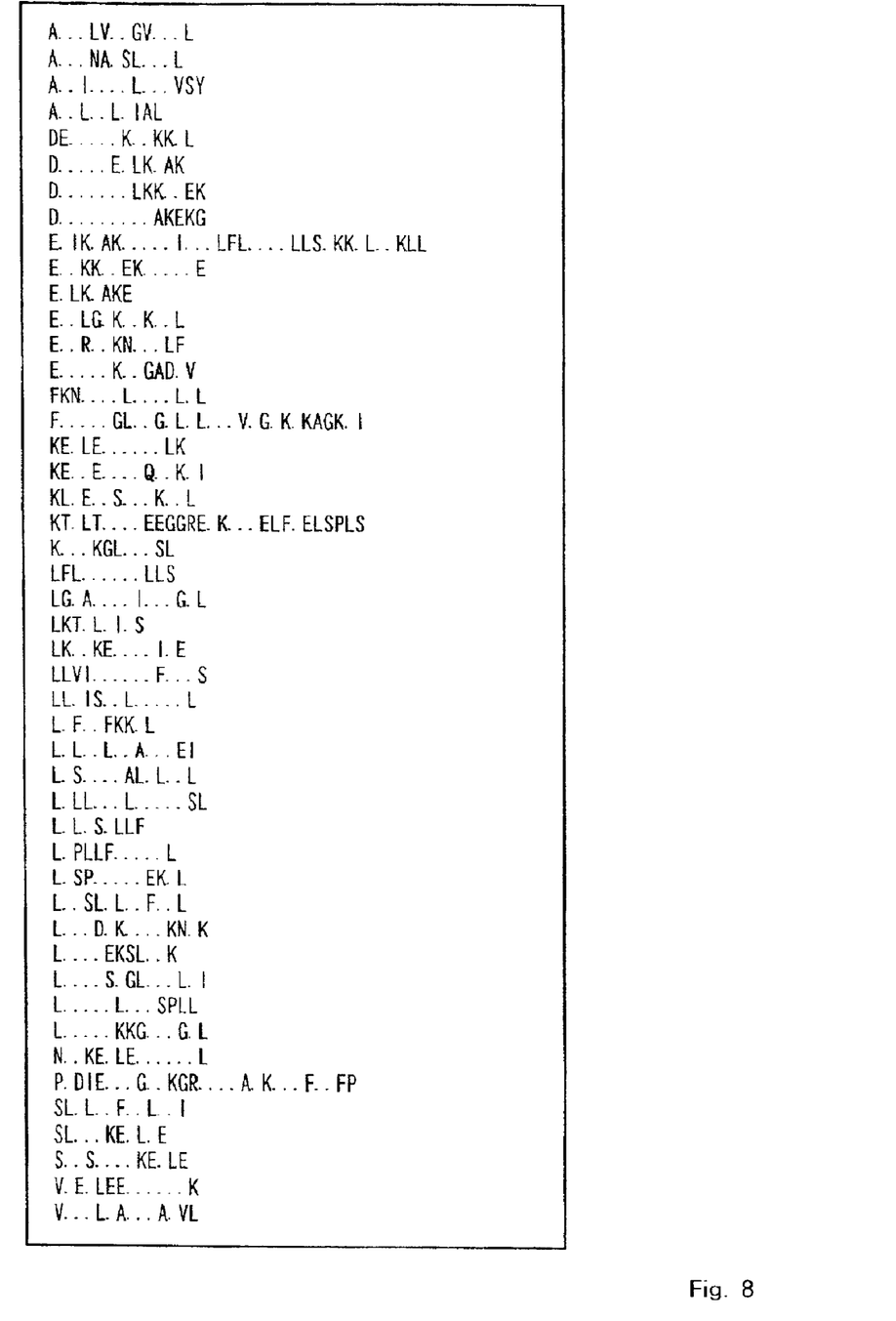
FIG. 8 is an example database 11 containing multiple protein patterns.

FIG. 8 is an example database 11 containing multiple protein patterns. Protein patterns shown in FIG. 8 are also called motifs. It is noted that a symbol "." shown in patterns may be any character.

Let's consider a search system (database server 10) that answers all the patterns in database 11 that are included in a query sequence subjected to a query when performing database search on database 11 shown in FIG. 8 using any protein sequence as a query. For example, assuming that a query is issued using the protein sequence "TAAELCTLVI-ALGA" as the query sequence, a pattern "A..L..L.IAL" in database 11 appears in this query sequence beginning from the second character. Accordingly, database server 10 returns this pattern as search results.

Figure 9:
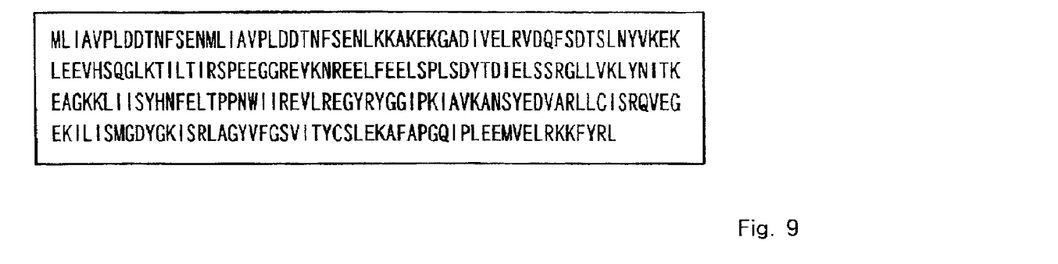
FIG. 9 depicts a protein sequence of coliform bacillus (accession number: gi2982763).

FIG. 9 depicts a protein sequence of coliform bacillus (accession number: gi2982763).

Now let's consider when issuing a query to database server 10 having database 11 shown in FIG. 8 using the protein sequence shown in FIG. 9 as a query sequence.

Figure 10:
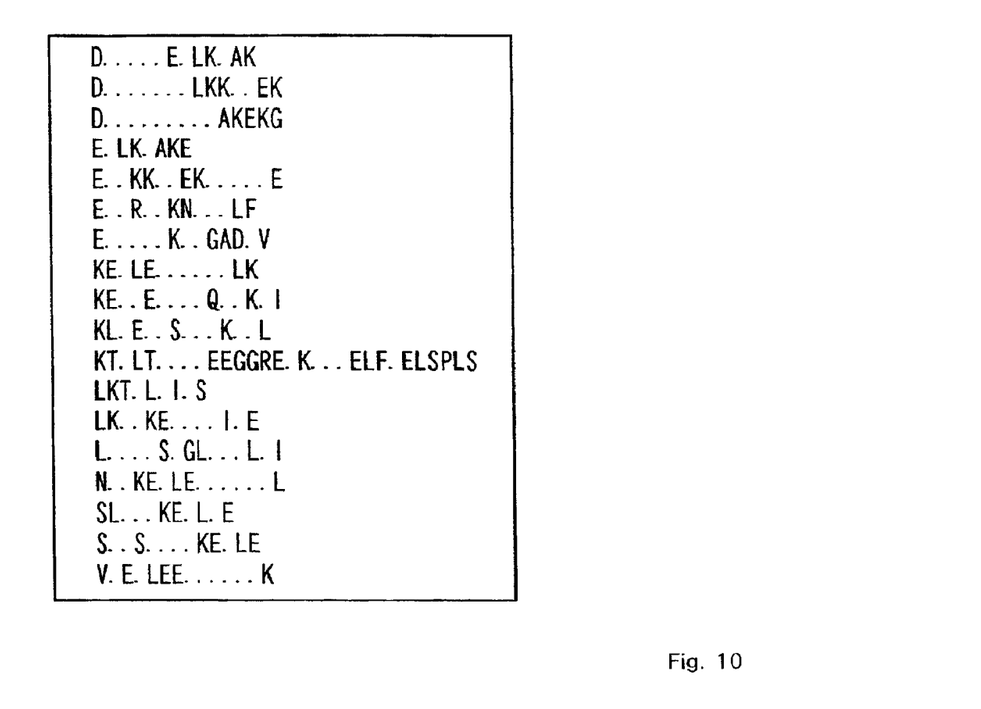
FIG. 10 depicts answers as a result of issuing a query to database shown in FIG. 8 using a sequence of FIG. 9 as a query sequence.

FIG. 10 depicts answers (search results) to this query from database server 10.

As shown in FIG. 10, database server 10 returns 18 patterns based on database 11 shown in FIG. 8 in response to the query that uses the protein sequence shown in FIG. 9 as a query sequence.

In this embodiment of the invention, client 20, which wants to perform database search as described above, processes the sequence shown in FIG. 9 using techniques (1) through (5) and then issues queries to database server 10 using the resultant sequences as query sequences.

Referring to the flowchart shown in FIG. 6, sequence processing section 21 in client 20 first inputs the protein sequence of FIG. 9 as a search sequence (step 601), then divides this protein sequence using the technique (1) described above (step 602). In doing so, other search sequences or dummy sequences may be connected before dividing the protein sequence, as described in the technique (5).

Next, sequence processing section 21 may create dummy sequences and add them to multiple divided sequences created in step 602, if needed, using the technique (2), (3) or (4) (step 603).

Figure 11:
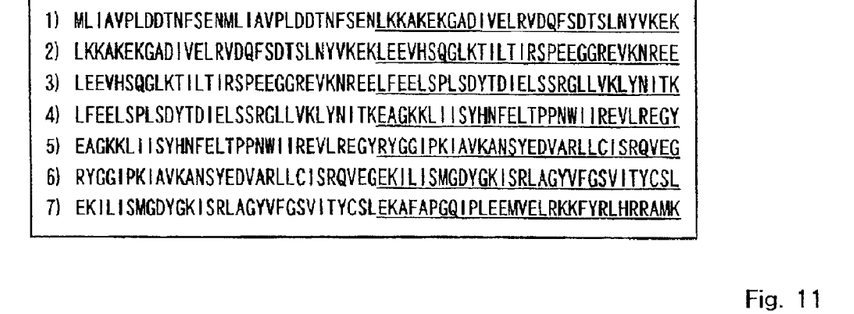
FIG. 11 depicts an example sequence created as a result of processing the protein sequence shown in FIG. 9.

FIG. 11 depicts an example sequence created as a result of processing the protein sequence shown in FIG. 9.

In this example shown in FIG. 11, the protein sequence of FIG. 9 is divided into sequences with a length of 60 each of which has an overlapped portion of 30 bases respectively. It is seen in FIG. 11 that the last half of each sequence underlined overlaps with the first half of the next sequence not underlined, respectively. Furthermore, a random character string "HRRAMk" is added to the seventh sequence to make the length of it 60 in order to make it impossible to identify the seventh sequence as the last sequence.

It is noted that as described above in relation to the technique (1) for processing a sequence, assuming the maximum length of patterns stored in database 11 is m, the length of the overlapped portion Ai is to be more than or equal to m-1. Namely, it is assumed here that m≦31 for database 11 shown in FIG. 8.

While a partial character string Bi is an empty sequence and the length of sequences is 60 in the above example, the partial character string Bi may be set randomly to make the length of each sequence uneven. This makes it unnecessary to add a meaningless character string at the end of the seventh sequence in order to make it impossible to identify the seventh sequence being the last sequence.

Then, query issuing section 22 creates queries using the sequences (1) through (7) shown in FIG. 11 created by sequence processing section 21 as query sequences, and then transmits them to database server 10 (step 604). It is noted that the queries for all the multiple query sequences created may be transmitted collectively at a time or in several times.

Database server 10 performs database search in response to multiple query sequences for queries received from client 20 and sends back the search results to client 20. With respect this database search, since the length of overlapped portions of query sequences (1) through (7) is 30, the search is performed on all of the patterns with the length of less than or equal to 30 included in the original sequence (protein sequence of FIG. 9). As mentioned above, database server 10 shown in FIG. 8 does not include any pattern with the length of more than 31. Accordingly, all of the patterns in database 11 that are contained in the original sequence are searched by performing database search on sequences (1) through (7).

Now referring to FIG. 7, information extracting section 23 receives the search results from database server 10 (step 701), and then extracts and outputs the search results corresponding to the sequences of FIG. 9 (step 702).

Figure 12:
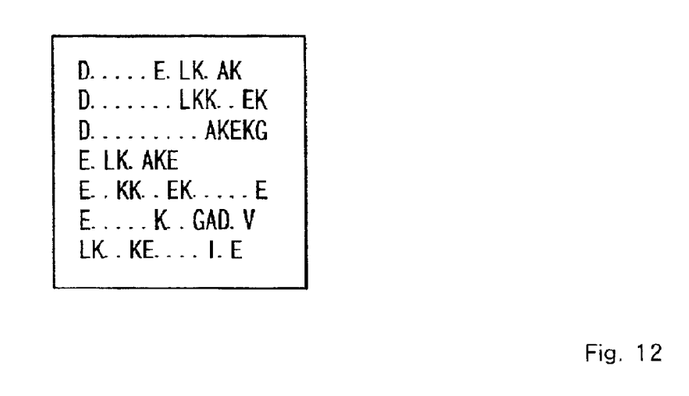
FIG. 12 depicts search results sent back from database server 10 corresponding to sequence (1) shown in FIG. 11.

FIG. 12 depicts the search results sent back from database server 10 corresponding to sequence (1) shown in FIG. 11. Namely, it is seen that seven kinds of patterns are included in sequence (1). Information extracting section 23 collects the search results sent back corresponding to each of the sequences (1) through (7) and outputs them as the search results for the protein sequence of FIG. 9 serving as a search sequence. It is noted that since sequence (7) includes the meaningless character string "HRRAMK" at its end, any patterns matching with this portion are to be excluded.

As mentioned above, according to the present invention, it is difficult for someone except for client 20 who knows an original search sequence to restore the original search sequence from query sequences subjected to queries. Therefore, it effectively prevents an owner of database 11 or someone who intercepts on the network 30 from knowing on what sequence client 20 is performing database search. Moreover, according to the invention, client 20 processes the search sequence and further processes the search results sent back from database server 10 in consideration of the processing applied to, thus the same search results can be obtained as in the case when performing database search directly on this search sequence. Accordingly, there is no need to change the design of database 11 and database server 10 containing it. Consequently, the database search method according to the present invention can be easily introduced into existing database search systems.

Hereinbefore, there has been described the database search wherein the protein sequence of FIG. 9 is divided using the technique (1) mentioned above. According to the invention, it is also possible to issue a query with adding various sequences to the seven sequences (1) through (7) of FIG. 11 using the techniques (2) through (4) mentioned above.

Figure 13:
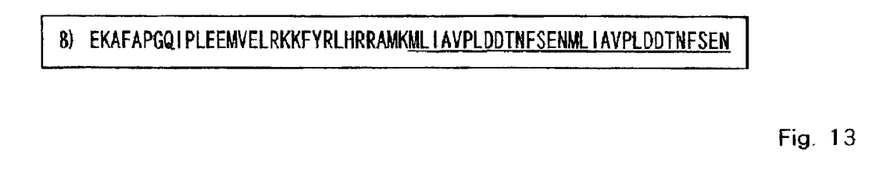
FIG. 13 depicts an example sequence created by using technique (2) according to the invention.

For example, using the technique (2), it is possible to add a sequence (8) shown in FIG. 13 to the seven sequences of FIG. 11. With respect to the sequence (8) of FIG. 13, the first part of it (not underlined) overlaps with the last part of the sequence (7) of FIG. 11 (underlined), while the last part (underlined) overlaps with the first part of the sequence (1) (not underlined). Accordingly, by adding this sequence (8) to the sequences (1) through (7) shown in FIG. 11 and performing database search, even if someone acquires all the search results corresponding to the sequences (1) through (8), he can not understand which sequence (1) through (8) the head of the original sequence (i.e., protein sequence of FIG. 9) is, therefore, he can not obtain correct search results unless he knows the original sequence.

Besides, using the technique (3), the following sequences can be created.

Figure 14:
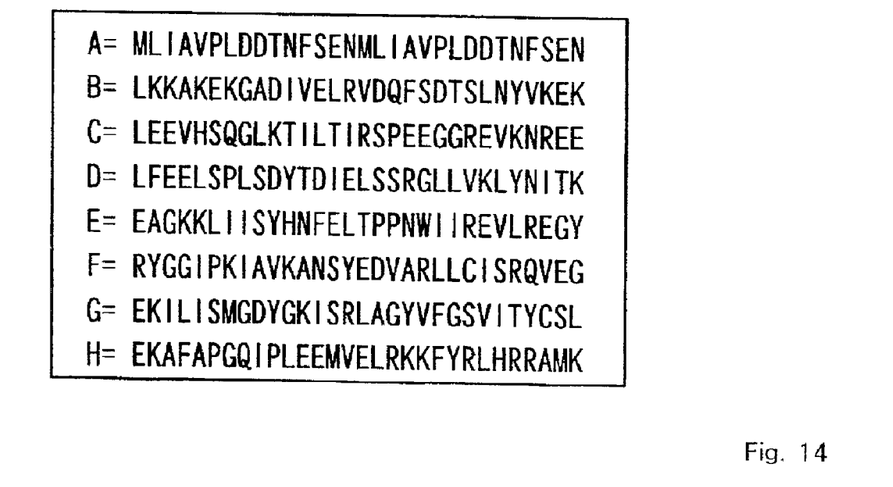
FIG. 14 depicts example sequences created by using technique (3) according to the invention.

First, the protein sequence of FIG. 9 is divided into eight partial character strings A through H with the length of 30 shown in FIG. 14. It is noted that like the sequence (7) shown in FIG. 11, the meaningless character string "HRRAMK" is appended at its end to uniform the length of theses character strings.

Then, for each of the character strings shown in FIG. 14, it is assumed that the following 48 kinds of sequences are created.

A+C, A+D, A+E, A+F, A+G, A+H,
B+A, B+D, B+E, B+F, B+G, B+H,
C+A, C+B, C+E, C+F, C+G, C+H,
D+A, D+B, D+C, D+F, D+G, D+H,
E+A, E+B, E+C, E+D, E+G, E+H,
F+A, F+B, F+C, F+D, F+E, F+H,
G+A, G+B, G+C, G+D, G+E, G+F,
H+B, H+C, H+D, H+E, H+F, H+G (Note that A+C represents a sequence created by connecting character strings A and C, for example. While such sequences as A+A or B+B, that is, sequences created by connecting the same character string are not shown here, those sequences may be created as necessary.) After adding the above sequences to the eight sequences including sequences (1) through (7) of FIG. 11 and a sequence (8) of FIG. 13, queries are to be created.

In this way, since the sequences having A as a character string of the first half include seven kinds, that is, A+B, A+C, A+D, A+E, A+F, A+G, A+H, there is no way to know which character string essentially follows the character string A. Consequently, the number of possible combinations of sequences created by combining these is 40320 (=8!), thus it is extremely difficult to restore the original sequence after collecting the search results for all the queries.

Now consider the case where only eight sequences, A+C, B+D, C+E, D+F, E+G, F+H, G+A, H+B, are added corresponding to the sequences (1) through (7) of FIG. 11, respectively, rather than adding all the above 48 kinds of sequences, wherein the character string A+C is added to the sequence (1) of FIG. 11 (that corresponds to a sequence A+C using the character string of FIG. 13), for example. Even in this case, there are two kinds of sequences, A+B and A+C, that have the character string A as a character string of the first half, wherein there is no way to know which character string is correct. Accordingly, the number of possible combinations of sequences created by combining these is 496, thus it is also difficult to restore the original sequence after collecting the search results for all the queries.

Figure 15:
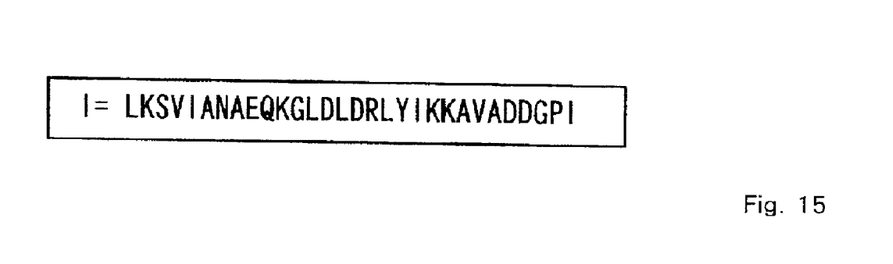
FIG. 15 depicts an example sequence created by using technique (4) according to the invention.

Moreover, it is also possible to create a character string I with the length of 30 shown in FIG. 15 using the above technique (4) and then add dummy sequences such as A+I and I+D to the sequences (1) through (7) of FIG. 11, thereby making it difficult to restore the original sequence.

While not showing a specific example, connecting other sequences to the protein sequences of FIG. 9 using the technique (5) prior to dividing the protein sequence of FIG. 9 using the technique (1) makes it much more difficult to acquire the search results for the protein sequence of FIG. 9 after collecting the search results for queries.

As mentioned above, according to the present invention, there is provided a method for allowing database search, which prevents an owner of the database or someone who intercepts the database search halfway through the network from knowing the contents of a query, without requiring any particular processing on the part of a database.

As mentioned above, the present invention implements database search that hides the contents of a query against an owner of a database or someone who intercepts on the network without requiring design changes, thus being easily introduced in existing database search systems.

What is claimed is:

1. A database search device for accessing a database that stores sequence patterns and inquiring whether the sequence patterns stored in the database exist in a predetermined sequence, the device comprising:

a sequence processing section for inputting an original search sequence, dividing the original search sequence into multiple subsequences, adding dummy subsequences, and adding and overlapping the subsequences and the dummy subsequences to create a query sequence and hide the original search sequence;

a query issuing section for issuing a query to said database using said created query sequence; and an information extracting section for receiving and analyzing a response to the query issued from the query issuing section, and extracting and outputting information corresponding to search results for the original sequence.

2. The database search device according to claim 1, wherein said sequence processing section overlaps a predetermined length of sequence elements depending on a length of the sequence patterns stored in said database to create said multiple subsequences.

3. The database search device according to claim 1, wherein said sequence processing section creates a sequence by connecting a sequence element of an end portion of said original search sequence and a sequence element of a head portion of said original search sequence and adds to said subsequences.

4. The database search device according to claim 1, wherein said sequence processing section creates a dummy sequence that does not contribute to database search associated with said original search sequence and adds to said subsequences.

5. A database search device for accessing a database that stores sequence patterns and inquiring whether the sequence patterns stored in the database exist in a predetermined sequence corresponding to an original sequence, the device comprising:

means for dividing the original sequence into multiple subsequences, means for creating dummy sequences;

means for combining said subsequences and dummy sequences into a query sequence, said query sequence hiding the original sequence;

means for making an inquiry multiple times to said database about the query sequence subjected to search, each of the inquires corresponding to each of subsequences of the original search sequence;

and means for receiving search results from said database and extracting information corresponding to said original sequence from the search results.

6. The database search device according to claim 5, wherein said means for making an inquiry overlaps a predetermined length of subsequences depending on a length of the sequence patterns stored in said database to create multiple subsequences of the search sequence, and makes an inquiry to the database for each of the created subsequences.

7. A database search system, comprising:

a database server provided on a network for storing predetermined sequence patterns;

and a client for making an inquiry about an original search sequence to the database server via said network, wherein said client divides the original search sequence subjected to search into a plurality of subsequences, adds dummy sequences thereto, adding and overlapping said subsequences and dummy sequences to form a guery sequence hiding said original search sequence, and sends the query sequence to said database server to search for each of said subsequences within said query sequence, wherein said database server performs a database search in response to the received query and sends back search results to said client; and wherein said client further receiving and analyzing the search results, extracting and outputting information corresponding to search results for the original search sequence.

8. A program for controlling a computer to access a database that stores sequence patterns and to inquire whether the sequence patterns stored in the database exist in a predetermined sequence corresponding to an original search sequence, comprising:

sequence processing means for dividing the original search sequence into multiple subsequences, adding dummy sequences thereto, adding and overlapping the subsequences and dummy sequences to form a query sequence and hide the original search sequence;

query issuing means for issuing a query to said database using created multiple subsequences individually as said query sequence and means for receiving search results from said database and extracting information corresponding to said original sequence from the search results.

9. The program according to claim 8, wherein said sequence processing means creates a dummy sequence that does not contribute to database search associated with said search sequence, and wherein said query issuing means issues a query to said database using said dummy sequence as a query sequence.

10. The program according to claim 8, wherein said sequence processing means connects any sequence to the search sequence to create a new sequence prior to dividing said search sequence and divides said created new sequence to create the multiple subsequences.

11. A storage media for storing a program for controlling a computer to access a database that stores sequence patterns and to inquire whether the sequence patterns stored in the database exist in a predetermined sequence corresponding to an original search sequence, the program comprising:

sequence processing means for dividing the original search sequence into multiple subsequences, adding dummy sequences thereto, adding and overlapping the subsequences and dummy sequences to form a query sequence and hide the original search sequence;

query issuing means for issuing a query to said database using created multiple subsequences individually as said query sequence;

and means for receiving search results from said database and extracting information corresponding to said original sequence from the search results.

* * * * *